(12) United States Patent
Jugl et al.

(10) Patent No.: US 9,592,341 B2
(45) Date of Patent: Mar. 14, 2017

(54) ARRANGEMENT FOR USE IN A DRUG DELIVERY DEVICE

(75) Inventors: Michael Jugl, Frankfurt am Main (DE); Günther Sendatzki, Frankfurt am Main (DE); Axel Teucher, Frankfurt am Main (DE); Axel Forstreuter, Frankfurt am Main (DE); Rainer Dönig, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 593 days.

(21) Appl. No.: 13/500,413

(22) PCT Filed: Oct. 14, 2010

(86) PCT No.: PCT/EP2010/065445
§ 371 (c)(1),
(2), (4) Date: Sep. 17, 2012

(87) PCT Pub. No.: WO2011/045386
PCT Pub. Date: Apr. 21, 2011

(65) Prior Publication Data
US 2013/0006191 A1    Jan. 3, 2013

(30) Foreign Application Priority Data

Oct. 16, 2009   (EP) ..................................... 09173305
Dec. 11, 2009   (EP) ..................................... 09178819

(51) Int. Cl.
*A61M 5/24*     (2006.01)

(52) U.S. Cl.
CPC ....... *A61M 5/24* (2013.01); *A61M 2005/2407* (2013.01); *A61M 2005/2474* (2013.01); *A61M 2005/2477* (2013.01)

(58) Field of Classification Search
CPC ............ A61M 5/24; A61M 2005/2403; A61M 2005/2407; A61M 2005/2474;
(Continued)

(56) References Cited

U.S. PATENT DOCUMENTS 2,157,503 A    5/1939   Smith
4,664,656 A *   5/1987   Taddei ........................ 604/241
(Continued)

FOREIGN PATENT DOCUMENTS

| EP | 0787501 | 8/1997 |
|---|---|---|
| GB | 272742 | 6/1927 |
| WO | 92/04926 | 4/1992 |

OTHER PUBLICATIONS

International Search Report for International App. No. PCT/EP2010/065445, completed Apr. 29, 2011.
(Continued)

*Primary Examiner* — Theodore Stigell
*Assistant Examiner* — Benjamin Koo
(74) *Attorney, Agent, or Firm* — McDonnell Boehnen Hulbert & Berghoff LLP

(57) ABSTRACT

The present invention relates to an arrangement for use in a drug delivery device comprising a cartridge holder, the cartridge holder comprising an opening at its distal end, a needle holder and one or more intermediate elements, wherein when the needle holder is mounted to the cartridge holder and the one or more intermediate elements are arranged in the opening of the cartridge holder whereby the size of the free space within the opening is reduced. Furthermore, it relates to a drug delivery device which is comprising such an arrangement and to a method for stabilizing a septum located at the distal end of a medicament cartridge.

11 Claims, 2 Drawing Sheets

(58) Field of Classification Search
CPC .. A61M 2005/2477; A61M 2005/2488; A61M 2005/247
See application file for complete search history.

(56) References Cited

U.S. PATENT DOCUMENTS

| | | | | |
|---|---|---|---|---|
| 5,334,162 | A * | 8/1994 | Harris | A61J 1/062 604/232 |
| 5,356,383 | A * | 10/1994 | Daly | A61M 5/24 206/366 |
| 6,068,616 | A * | 5/2000 | Janus | A61M 5/24 604/187 |
| 6,126,646 | A * | 10/2000 | Hansen | A61M 5/24 604/232 |
| 2006/0264898 | A1 * | 11/2006 | Beasley et al. | 604/506 |

OTHER PUBLICATIONS

International Preliminary Report on Patentability for International App. No. PCT/EP2010/065445, completed Mar. 2, 2012.

* cited by examiner

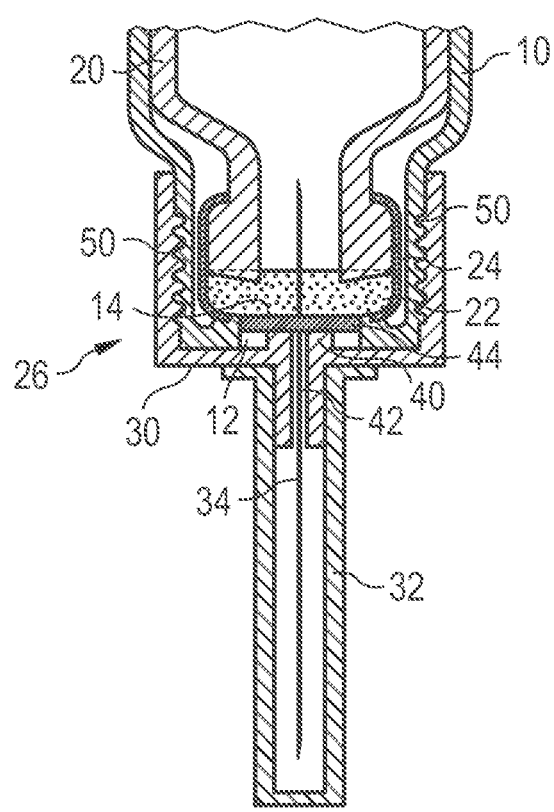

ARRANGEMENT FOR USE IN A DRUG DELIVERY DEVICE

CROSS REFERENCE TO RELATED APPLICATIONS

The present application is a U.S. National Phase Application pursuant to 35 U.S.C. §371 of International Application No. PCT/EP2010/065445 filed Oct. 14, 2010, which claims priority to European Patent Application No. 09173305.5 filed on Oct. 16, 2009 and European Patent Application No. 09178819.0 filed on Dec. 11, 2009. The entire disclosure contents of these applications are herewith incorporated by reference into the present application.

FIELD OF INVENTION

The present invention relates to an arrangement for use in a drug delivery device.

BACKGROUND

Drug delivery devices are generally known for the administration of a medicinal product, for example insulin, but also for other medicinal products for self-administration by a patient. Therefore, the drug delivery devices should be safe and comfortable in use and should dispense an exact dose of a medicinal product. Most of the drug delivery devices are pen type injectors, which can dispense a pre-set dose of a medicinal product.

In some cases, it is necessary for the patient to get an exact volume of a certain medicinal product. In most commercially available drug delivery devices, there are many sources of error for dispensing inaccuracy. One is for example the dripping out of the needle after injection and therefore the need to keep the needle in the skin after injection.

SUMMARY

It is an object to the present disclosure to provide an arrangement for use in a drug delivery device, which helps to improve the accuracy of a dispensed dose.

According to a first aspect of the present disclosure, an arrangement for use in a drug delivery device is provided, wherein the arrangement comprises a needle holder, a cartridge holder and one or more intermediate elements. The cartridge holder comprises an opening at its distal end. The needle holder is mountable to the cartridge holder, thereby arranging one or more intermediate elements in the opening of the cartridge holder. Due to the arrangement of the one or more intermediate elements, the free space within the opening is reduced.

The intermediate elements may be arranged at the cartridge holder or at the needle holder. When the needle holder is mounted to the cartridge holder, the one or more intermediate elements are arranged at the proximal end of the opening and are thereby reducing the free space within the opening.

The expressions proximal and distal are used to specify the directions of the drug delivery device, the assembly and the parts of the assembly, wherein the distal end is where the liquid medicinal product is dispensed and the proximal end is the opposite end of the distal end of the drug delivery device.

The proximal end of the opening at the distal end of the cartridge holder may be filled with one or more intermediate elements. If there are more intermediate elements, the elements are arranged such that there are no overlaps and no gaps between the intermediate elements. The arrangement preferably provides the intermediate elements with a smooth surface at the distal end of the opening. Preferably, there is just one opening through which a needle can pass.

In a preferred embodiment, at least one of the one or more intermediate elements comprises at least one opening through which a needle can pass.

The needle holder comprises a needle. When the needle holder is mounted to the cartridge holder, the assembled needle punctures a septum located at the distal end of an assembled medicament cartridge. To enable the needle to puncture the septum, an opening is located at the at least one intermediate element through which the needle can pass. The medicament cartridge may have the form of a container which is filled with a medicament, preferably a medicament in fluid form.

In another preferred embodiment, one or more intermediate elements are capable of forming a stabilizing support for a septum located at a distal end of a medicament cartridge, which is mounted to the cartridge holder.

Thus, due to the arrangement of the intermediate elements at the proximal end of the opening, a septum is provided with a stabilizing support. At least a face of the one or more intermediate elements is abutting against the septum and is thereby supporting the septum by forming a rigid board.

The rigid board provides the septum to withstand or reduce a bending due to a pressure which is exerted onto the septum while a bung is moved forwards in the medicament cartridge.

In another preferred embodiment, the one or more intermediate elements are arranged at the needle holder.

There are many possible ways to arrange the one or more intermediate elements. One way is to arrange at least one of the one or more intermediate elements at the needle holder.

The one or more intermediate elements can be located near the needle holder, inserted in the needle holder or can be integrally formed with the needle holder.

The one or more intermediate elements might be cylindrically shaped. The cylindrically shaped intermediate element may be located in the centre of the needle holder. There may be an opening in the middle of the intermediate element, through which a needle can pass.

When the needle holder is mounted to the cartridge holder, the cylindrically shaped intermediate element of the needle holder fits into the opening at the distal end of the cartridge holder. Thereby the opening can be reduced such that only one opening is left through which a needle can pass.

Generally, it can be said that the one or more intermediate elements can have the same shape as the opening at the distal end of the cartridge holder. Due to the fitting shapes of the one or more intermediate elements and the opening, a closed surface is formed between the one or more intermediate elements and the cartridge holder.

According to another embodiment, the one or more intermediate elements are arranged at the cartridge holder.

At least one of the intermediate elements may be arranged at the cartridge holder. Another possible way of forming a stabilizing support for a septum could be to arrange one intermediate element at the needle holder and another intermediate element at the cartridge holder such that both intermediate elements cooperate to abut and stabilize the septum.

The one or more intermediate elements can be located near the cartridge holder, inserted in the cartridge holder or can be integrally formed with the needle holder.

In another embodiment, a surface at the distal end of the cartridge holder is inclined to the opening located at the distal end of the cartridge holder.

The inclined surface extends and leads towards the septum. Therefore, the free space within the opening is reduced. An additional intermediate element may be arranged at the needle holder. This additional intermediate element can further reduce the free space within the opening along the axis.

In another preferred embodiment, the inclined surface of the cartridge holder is configured to simplify inserting a needle into the medicament cartridge.

Arranging a needle holder to the cartridge holder can be simplified by means of the inclined surface of the cartridge holder. The inclined surface leads the needle to pass the opening and puncture the septum of an assembled medicament cartridge.

According to one preferred embodiment, one of the one or more intermediate elements is a grid. The grid may comprise fibers.

The grid can be for example located at the proximal end of the opening. The grid abuts the septum of an assembled medicament cartridge. Due to the location of the grid, the septum is receiving a stabilizing support.

In another preferred embodiment, the grid comprises fibers that evade a needle when a needle passes through the opening.

One may use natural fibers as well as synthetic fibers. Synthetic fibers are manufactured from synthetic materials such as petrochemicals.

In another preferred embodiment, one or more intermediate elements comprise a material which has a low compressibility.

Due to the low compressibility of the intermediate element, the septum can get stabilizing support. The stabilizing effect is still enhanced when the compressibility of the one or more intermediate element is decreased.

In one embodiment, one or more intermediate elements are formed to help a septum to withstand a bending through the pressure, which is exerted on the septum while a bung is moved forward in a medicament cartridge, which is mounted to the arrangement.

To dispense a dose of a medicinal product, the user pushes a bung in distal direction. Due to the movement of the bung, a pressure is exerted on the septum. Thereby, the septum is bent under the pressure. Due to the bending, the amount of the dispensed dose of a medicinal product is not always accurate. The intermediate elements are supporting the septum to withstand or at least to reduce the bending. This leads to more dose accuracy.

In another preferred embodiment, the needle holder and the cartridge holder are threadedly engaged.

The needle holder comprises an inner thread at its proximal end and the cartridge holder comprises an outer thread at its distal end. To assemble the needle holder and the cartridge holder, both threads are engaged.

In another preferred embodiment, the drug delivery device is configured to dispense a liquid medicinal product through an assembled needle, which is comprised in the needle holder.

The needle holder comprises a needle and a needle cap as protective casing for the needle. To use the drug delivery device, the needle cap is removed. The needle, which is comprised in the needle holder, punctures the septum of a medicament cartridge, thereby enabling the liquid medicinal product contained in the medicament cartridge to be dispensed.

According to a second aspect of the present disclosure, a method for stabilizing a septum located at the distal end of a medicament cartridge is provided, the medicament cartridge being located at an arrangement comprising a cartridge holder, the cartridge holder comprising an opening at the distal end, a needle holder and one or more intermediate elements. The method is comprising the following steps:

One or more intermediate elements are arranged in an opening at the distal end of a cartridge holder by mounting the needle holder to the cartridge holder. The position of the one or more intermediate elements is determined such that the size of the free space within the opening is reduced and at least one of the one or more intermediate elements comprises at least one opening through which a needle is passing. The one or more intermediate elements are thereby forming a stabilizing support for the septum.

In a preferred embodiment, one of the one or more intermediate elements is a grid, which is inserted or injected into the opening.

The grid can be arranged at the needle holder or at the cartridge holder. It may be inserted or injected. The grid may be injected, or the needle holder or the cartridge holder comprising the grid can be manufactured via injection molding.

In another preferred embodiment, the grid is arranged at a proximal end face of the opening at the cartridge holder.

One possible method for arranging the grid is to insert the grid into the cartridge holder where it is abutting the proximal end face of the opening.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

In the following, the invention is described in further details with reference to the drawings, wherein FIG. 3 shows a cross sectional view of a cartridge holder which is comprising a cartridge and an assembled needle holder, the cartridge holder having a grid which is located at a proximal end face of the opening at the distal end of the cartridge holder and the needle holder having another intermediate element arranged in the opening of the cartridge holder.

DETAILED DESCRIPTION

Some preferred embodiments of the arrangement according to the present disclosure will now be discussed with reference to FIG. 1, FIG. 2 and FIG. 3. Identical reference signs denote identical or comparable components.

Figure 1:
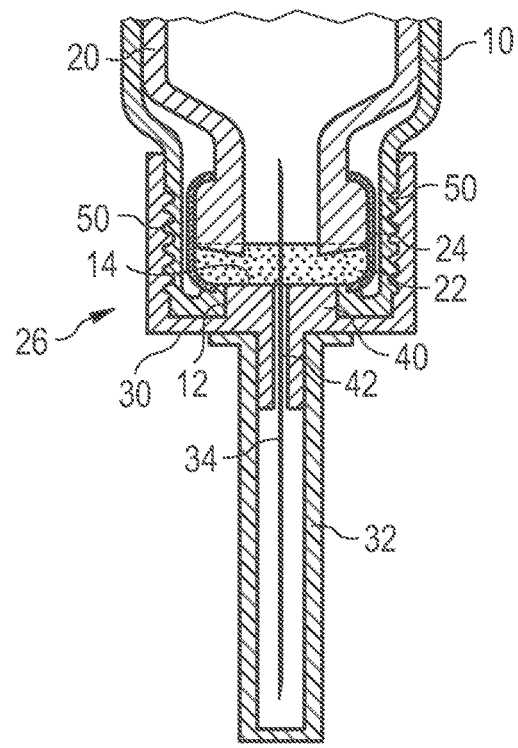
FIG. 1 shows a cross sectional view of a cartridge holder comprising a cartridge and an assembled needle holder comprising an intermediate element arranged in the opening of the cartridge holder.

FIG. 1 shows a cross sectional view of a cartridge holder 10 and an assembled needle holder 30. The needle holder 30 and the cartridge holder 10 are threadedly engaged 50. A medicament cartridge 20 is mounted to the cartridge holder 10.

The medicament cartridge 20 comprises a cap 24 bended over the distal end of the medicament cartridge 20, wherein the cap 24 is retaining a septum 22 at the distal end 26 of the medicament cartridge 20.

The needle holder 30 comprises an intermediate element 40, a needle 34 and a needle cap 32 seated over the distal end of the needle 34. The proximal end of the needle 34 punctures the septum 22, whereby the needle 34 gets in contact with the fluid medicinal product contained in the medicament cartridge 20.

The intermediate element 40 is arranged in the opening 12 at the distal end of the cartridge holder 10. In the middle of the intermediate element 40, an opening 42 is shown through which the needle 34 passes. The inner lateral area of the opening 12 at the distal end of the cartridge holder 10 is in contact with the lateral area of the intermediate element 40 which is located at the needle holder 30.

The proximal end face of the intermediate element 40 is abutting the septum 22. Thereby, a stabilizing support for the septum 22 is achieved which helps the septum 22 to withstand a bending through the pressure which is exerted on the septum 22 while a bung, which is not shown in the figure, is moved forward in a medicament cartridge 20.

Figure 2:
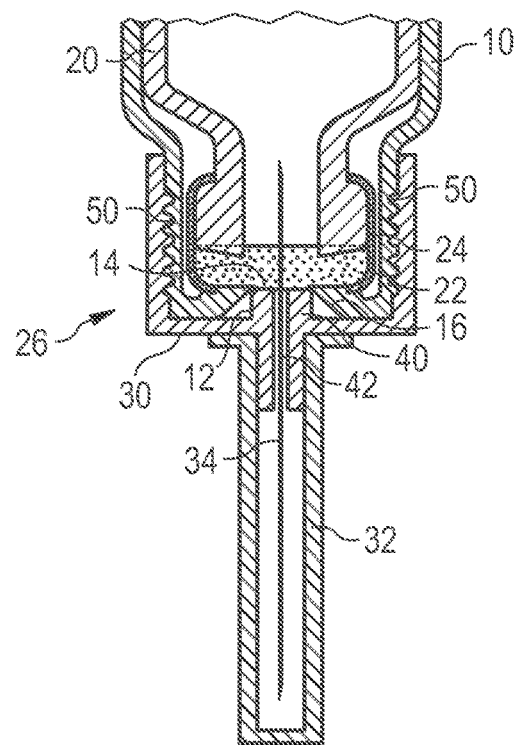
FIG. 2 shows a cross sectional view of a cartridge holder which is comprising a cartridge and an assembled needle holder, the cartridge holder having an inclined surface and an intermediate element at the needle holder arranged in the opening of the cartridge holder.

FIG. 2 shows a similar arrangement as shown in FIG. 1 with the difference that the cartridge holder 10 is inclined towards the proximal end of the opening 12 at the distal end of the cartridge holder 10, thereby reducing the free space within the opening 12. The first intermediate element 16 is inclined and is located at the cartridge holder 10.

Additionally, the inclined surface 16 leads the needle 34 to pass the opening 12 and helps to puncture the septum 22 of an assembled medicament cartridge 20.

Additionally, a second intermediate element 40 is located in the middle of the needle holder 30. The proximal rim of the intermediate element 40 at the needle holder 30 is abutting the incline 16. Furthermore, the proximal end face of the intermediate element 40 is abutting the septum 22.

Thereby, a stabilizing support for the septum 22 is achieved which helps the septum 22 to withstand a bending through the pressure which is exerted on the septum 22 while a bung, which is not shown, is moved forward in a medicament cartridge 20.

FIG. 3 shows a similar arrangement as shown in FIG. 1 with the difference that a first intermediate element located at the cartridge holder 10 is a grid 44. The grid 44 is located at the proximal end of the opening 12 at the distal end of the cartridge holder 10.

The needle holder 30 comprises in its middle a second intermediate element 40 whose proximal end face is supporting and abutting the grid 44.

Due to the arrangement of the first 44 and the second intermediate element 40, a stabilizing support for the septum 22 is achieved, which helps the septum 22 to withstand a bending through the pressure, which is exerted on the septum 22 while a bung, which is not shown, is moved forward in a medicament cartridge 20.

The present examples and embodiments are to be considered as illustrative and not restrictive, and the invention is not to be limited to the details given herein, but may be modified within the scope and equivalence of the appended claims.

The invention claimed is:

1. An arrangement for use in a drug delivery device comprising a cartridge holder, the cartridge holder comprising a sidewall with an outer surface and comprising a distal face with a first opening, wherein an outer thread extends along the outer surface near a distal end of the cartridge holder, a needle holder comprising a separate first intermediate element and a second intermediate element, the second intermediate element having a proximal end face and a second opening at a proximal end to receive the distal end of the cartridge holder, wherein the proximal end of the needle holder comprises a sidewall that defines an inner surface, wherein an inner thread extends along the needle holder inner surface, and the separate first intermediate element having the same shape and size as the first opening, being positioned in the opening and held in place when the needle holder is threadedly engaged with cartridge holder such that the proximal end face of the second intermediate element abuts the first intermediate element causing the first intermediate element to abut and form a stabilizing support for a septum located at a distal end of a medicament cartridge when the medicament cartridge is positioned within the cartridge holder, the abutting first intermediate element forming a closed surface adjacent the distal end of the cartridge holder.

2. An arrangement according to claim 1, wherein the first intermediate element comprises at least one opening through which a needle can pass.

3. An arrangement according to claim 1, wherein first intermediate element is a grid.

4. An arrangement according to claim 3, wherein the grid comprises fibers that evade a needle when a needle is passed through the opening.

5. An arrangement according to claim 1, wherein the first intermediate element comprises a material which has a low compressibility.

6. An arrangement according to claim 1, wherein the first intermediate element is formed to help a septum to withstand a bending through the pressure which is exerted on the septum while a bung is moved forward in a medicament cartridge which is mounted to the arrangement.

7. A drug delivery device comprising an arrangement according to claim 1, wherein the drug delivery device is configured to dispense a liquid medicinal product through an assembled needle which is comprised in the needle holder.

8. An arrangement according to claim 1, wherein the first intermediate element forms a stabilizing axial support for the septum of the cartridge.

9. A method for stabilizing a septum located at the distal end of a medicament cartridge, the medicament cartridge being located at an arrangement comprising a cartridge holder, the cartridge holder comprising a sidewall with an outer surface and comprising a distal face with a first opening, wherein an outer thread extends along the outer surface near a distal end of the cartridge holder, a needle holder comprising a separate first intermediate element and a second intermediate element, the second intermediate element having a proximal end face and a second opening at a proximal end to receive the distal end of the cartridge holder, wherein the proximal end of the needle holder comprises a sidewall that defines an inner surface, wherein an inner thread extends along the needle holder inner surface, the method comprising the steps of:

providing the first intermediate element having the same shape and size as the first opening, arranging the first intermediate element in the first opening at the distal end of the cartridge holder and holding the first intermediate element in place by mounting the needle holder to the cartridge holder such that the needle holder and the cartridge holder are threadedly engaged such that the proximal end face of the second intermediate element abuts the first intermediate element, whereby the position of the first intermediate element is determined such that the size of the free space within the first opening is reduced and wherein the first intermediate element forms a stabilizing support for the septum, such that a closed surface between the first intermediate element and the cartridge holder is formed and such that a face of the first intermediate element is abutting the septum located at a distal end of the medicament cartridge when the medicament cartridge is positioned within the cartridge holder.

10. A method according to claim 9, wherein the first intermediate element is a grid which is inserted or injected into the opening.

11. A method according to claim 10, wherein the grid is arranged at a proximal end face of the opening of the cartridge holder.

* * * * *